United States Patent [19]

O'Neill et al.

[11] 4,300,580
[45] Nov. 17, 1981

[54] HAIR GROOMING METHOD USING LINEAR POLYESTERS

[75] Inventors: George J. O'Neill; Allan R. Rothwell, both of Kingsport, Tenn.

[73] Assignee: Eastman Kodak Company, Rochester, N.Y.

[21] Appl. No.: 757,709

[22] Filed: Jan. 7, 1977

[51] Int. Cl.³ .................... A45D 7/00; A61K 7/06
[52] U.S. Cl. ............................ 132/7; 424/DIG. 2; 424/10; 424/11
[58] Field of Search ....... 132/7; 424/DIG. 1, DIG. 2, 424/70, 71, 47

[56] References Cited

U.S. PATENT DOCUMENTS

| | | | |
|---|---|---|---|
| 3,234,098 | 2/1966 | Sender et al. | 424/71 |
| 3,320,212 | 5/1967 | Shen et al. | 424/71 X |
| 3,734,874 | 5/1973 | Kibler et al. | 260/29.2 E |
| 3,779,993 | 12/1973 | Kibler et al. | 260/29.2 E |
| 3,937,802 | 2/1976 | Fujimoto et al. | 424/47 |
| 3,972,336 | 8/1976 | Nowak et al. | 132/7 |

*Primary Examiner*—Natalie Trousof
*Assistant Examiner*—Vera C. Clarke
*Attorney, Agent, or Firm*—John F. Stevens; Daniel B. Reece, III

[57] ABSTRACT

A composition and method for grooming the hair are disclosed. The composition is soluble in water and mixtures of alcohol and water, and comprises a linear polyester derived from
(A) at least one dicarboxylic acid,
(B) at least one diol, at least 20 mole percent of said diol component being a poly(ethylene glycol) having the formula

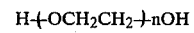

wherein n is an integer of from two to about ten, and
(C) a difunctional monomer containing a -SO₃M group attached to an aromatic nucleus, wherein M is hydrogen or a metal ion.

A preferred polyester is prepared from isophthalic acid, the sodium salt of 5-sulfoisophthalic acid, and a glycol component, at least a substantial portion of which is diethylene glycol. The composition may be used in solution, or blended with other compositions for use as a mixture therewith. Conventional additives, such as plasticizers, stabilizers, etc., may also be used. Hair is groomed by applying an effective amount of the composition thereto and allowing the solvent to evaporate from the polyester while maintaining the hair in place.

3 Claims, No Drawings

HAIR GROOMING METHOD USING LINEAR POLYESTERS

This invention relates to cosmetic compositions, and more specifically, this invention relates to hair grooming compositions comprising linear, water-dissipatable polyesters.

Hair grooming compositions are widely used at the present time to give human hair body, consistency, firm texture, and, in general, to maintain the hair in a desired arrangement for a certain length of time. Aerosol products are widely used, but the compositions may be in other forms such as aqueous or solvent solution, dispersion or suspension, wherein the liquid vehicle evaporates upon exposure to a particular atmosphere. Other forms of such compositions may be known to those skilled in the art.

Hair grooming compositions known in the art include those based on the ethyl ester of a polymethylvinylether and maleic anhydride copolymer, as well as polyvinyl pyrrolidinone and acrylates.

Hair grooming compositions should have sufficient tensile strength to support hair in desired arrangement, such as, for example, a curled arrangement. It is also necessary that hair grooming compositions have sufficient moisture resistance to withstand relative humidity in the area of 80-90% at a temperature of 70°-80° F., but the composition must be removable by normal washing procedures, such as by shampoo.

It is therefore an object of the present invention to provide a hair grooming composition meeting these requirements, and which is capable of being made available to the consumer at a reasonable cost.

It is another object of this invention to provide a hair grooming composition which may be used as a nonaerosol composition.

It is a further object of this invention to provide a method for grooming the hair.

Other objects of this invention will appear herein.

These and other objects are attained through the practice of this invention by use of a linear, water-dissipatable polyester derived essentially from components (A) at least one dicarboxylic acid, (B) at least one diol, at least 20 mole percent of said diol component being a poly(ethylene glycol) having the formula

wherein n is an integer of from two to about ten, and (C) a difunctional monomer containing a —$SO_3M$ group attached to an aromatic nucleus, wherein M is hydrogen or a metal ion. Such polyester compositions are described in U.S. Pat. Nos. 3,734,874 and 3,779,993, which are incorporated herein by reference. It is known to use such polyesters in sizing compositions for fibrous articles such as textile yarn, hemp rope, and tire cord, and as hot melt adhesives and protective coatings.

The term "dissipatable" will be understood to refer to the action of water or water/alcohol solution (preferably at least 25 percent by weight of water) on the polyester composition. This term is specifically intended to cover those situations wherein the polyester composition is dissolved or dispersed in water or an aqueous solution.

A preferred composition is prepared from isophthalic acid, the sodium salt of 5-sulfoisophthalic acid, diethylene glycol, and 1,4-cyclohexanedimethanol. In this composition, the isophthalic acid is hydrophobic, the sodium sulfoisophthalic acid is hydrophilic, the diethylene glycol is hydrophilic, and the 1,4-cyclohexanedimethanol is hydrophobic. This particular composition, when added to water, forms a dispersion which exhibits a "dispersion viscosity" higher than that of water but lower than that which might be expected if the polymer were completely dissolved. Thus, this particular composition acts as if it were partially soluble in water and partially insoluble, a behavior which is consistent with its hydrophobic-hydrophilic composition. In addition, the hydrophilic portion of the molecule can be increased and a completely water-soluble composition obtained. Conversely, the hydrophobic moiety of the polyester molecule can be increased and a composition which is water-dispersible but which imparts little or no additional viscosity to water can be used.

The dicarboxylic acid component from which the linear, water-dissipatable polyester composition is prepared can be any aliphatic, cycloaliphatic, or aromatic acid. Examples of such dicarboxylic acids include oxalic; malonic; dimethylmalonic; succinic; glutaric; adipic; trimethyladipic; pimelic; 2,2-dimethylglutaric; azelaic; sebacic; fumaric; maleic; itaconic; 1,3-cyclopentanedicarboxylic; 1,2-cyclohexanedicarboxylic; 1,3-cyclohexanedicarboxylic; 1,4-cyclohexanedicarboxylic; phthalic; terephthalic; isophthalic; 2,5-norbornanedicarboxylic; 1,4-naphthalic; diphenic; 4,4'-oxydibenzoic; diglycolic; thiodipropionic; 4,4'-sulfonyldibenzoic; and 2,5-naphthalenedicarboxylic acids. If terephthalic acid is used as the dicarboxylic acid component of the polyester, especially good results are achieved when at least five mole percent of one or the other acids listed above is used.

It should be understood that the use of the corresponding acid anhydrides, esters, and acid chlorides of these acids is included in the term "dicarboxylic acid". The esters are preferred, examples of which include dimethyl 1,4-cyclohexanedicarboxylate; dimethyl 2,6-naphthalenedicarboxylate; dibutyl 4,4'-sulfonyldibenzoate; dimethyl isophthalate; dimethyl terephthalate; and diphenyl terephthalate. Copolyesters may be prepared from two or more of the above dicarboxylic acids are derivatives thereof.

At least about 20 mole percent of the diol component used in preparing the polyester sizing composition is a poly(ethylene glycol) having the formula

wherein n is an integer of from two to about ten. Examples of suitable poly(ethylene glycols) include diethylene, triethylene, tetraethylene, pentaethylene, hexaethylene, heptaethylene, octaethylene, nonaethylene, and decaethylene glycols and mixtures thereof. Preferably the poly(ethylene glycol) employed in the polyester of the present invention is diethylene glycol, triethylene glycol or mixtures thereof. The remaining portion of the diol component is at least one aliphatic, cycloaliphatic, or aromatic diol. Examples of these diols include ethylene glycol; propylene glycol; 1,3-propanediol; 2,4-dimethyl-2-ethylhexane-1,3-diol; 2,2-dimethyl-1,3-propanediol; 2-ethyl-2-butyl-1,3-propanediol; 2-ethyl-2-isobutyl-1,3-propanediol; 1,3-butanediol; 1,4-butanediol; 1,5-pentanediol; 1,6-hexanediol; 2,2,4-trimethyl-1,6-hexanediol; 1,2-cyclohexanedimethanol; 1,3-cyclohexanedimethanol; 1,4-cyclohexanedimethanol; 2,2,4,4-tetramethyl-1,3-cyclobutanediol; and p-xylylenediol. Copolymers may be prepared from two or more of the above diols.

A third component used to prepare the polyester sizing composition is a difunctional monomer containing a —$SO_3M$ group attached to an aromatic nucleus, wherein M is hydrogen or a metal ion. This difunctional monomer component may be either a dicarboxylic acid (or derivative thereof) containing a —$SO_3M$ group or a diol containing a —$SO_3M$ group. The metal ion of the sulfonate salt group may be $Na^+$, $Li^+$, or $K^+$.

The —$SO_3M$ group is attached to an aromatic nucleus, examples of which include benzene, naphthalene, anthracene, diphenyl, oxydiphenyl, sulfonyldiphenyl, and methylenediphenyl.

Especially good results are obtained when the difunctional monomer is the sodium salt of a sulfoisophthalic, sulfoterephthalic, sulfophthalic, or 4-sulfonaphthalene-2,7-dicarboxylic acid (or derivatives of such acids). A highly preferred such monomer is 5-sodiosulfoisophthalic acid or a derivative thereof such as 5-sodiosulfodimethyl isophthalate. Another preferred difunctional monomer is 5-sodiosulfoisophthalic acid.

Other effective difunctional monomers containing a —$SO_3M$ group attached to an aromatic nucleus include metal salts of aromatic sulfonic acids (or esters thereof). These monomers have the general formula

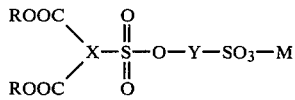

wherein X is a trivalent aromatic hydrocarbon radical, Y is a divalent aromatic hydrocarbon radical, R is hydrogen or an alkyl group of one to four carbon atoms, M is hydrogen, $Na^+$, $Li^+$, or $K^+$. Examples of preferred monomers here are 4-sodiosulfophenyl-3,5-dicarbomethoxybenzenesulfonate, 4-lithiosulfophenyl-3,5-dicarbomethoxybenzenesulfonate; and 6-sodiosulfo-2-naphthyl-3,5-dicarbomethoxybenzenesulfonate.

Other effective difunctional monomers containing a —$SO_3M$ group attached to an aromatic nucleus include metal salts of sulfodiphenyl ether dicarboxylic acids (or esters thereof). These monomers have the general formula

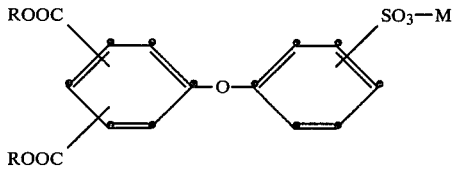

wherein R is hydrogen, an alkyl group of one to eight carbon atoms, or phenyl, and M is hydrogen, $K^+$, $Na^+$, or $Li^+$. These monomers are described, including methods for their preparation in Lappin et al. Defensive Publication, 868 O.G. 730, on Nov. 18, 1969. Examples of preferred monomers here are dimethyl 5-[4-(sodiosulfo)phenoxy]isophthalate, dimethyl 5-[4-(sodiosulfo)phenoxy]terephthalate, and 5-[4-(sodiosulfo)phenoxy]isophthalic acid.

When the difunctional monomer containing the —$SO_3M$ groups is an acid or derivative thereof (such as its ester), the polyester should contain at least about eight mole percent of the monomer based on total acid content, with more than ten mole percent giving particularly advantageous results. When the difunctional monomer is a diol, the polyester should also contain at least about eight mole percent of the monomer based on total diol content, with more than ten mole percent giving particularly advantageous results. Greater dissipatability is achieved when the difunctional monomer constitutes from about 12 mole percent to about 45 mole percent of the total content of acid or diol components of the polyester.

To obtain the polyester compositions of this invention, the difunctional monomer containing the —$SO_3M$ group may be added directly to the esterification reaction mixture from which the polyester will be made. Thus, these monomers can be used as a component in the original polyester reaction mixture. Other various processes which may be employed in preparing these sizing compositions are well known in the art.

The compositions will have an inherent viscosity (I.V.) of at least 0.15, as measured at 25° C. using 0.25 gram of polymer per 100 ml. of a solvent composed of 60 percent phenol and 40 percent tetrachloroethane.

Various additives may be incorporated into the compositions to achieve specific results. Examples of such additives include dyes, other pigments, stabilizers, and plasticizers.

The grooming compositions of this invention may be used in the following manner: the polyester, in powder or pellet form, is added to water or alcohol/water mixture at any convenient temperature between somewhat below room temperature to about 80° C. and is subjected to mild agitation. Depending upon the specific properties of the particular composition being used, a clear to cloudy, moderately viscous, stable dissipation is obtained.

The composition is applied to the hair in an effective amount, i.e., enough to "wet" the hair. Spraying, by nonaerosol, is a preferred method of application.

The polymers used in this invention may be blended with certain other substances which are compatible therewith. Substances may be used which increase the hardness and reduce the tackiness of the polymers of this invention. Other added substances have the opposite effect. Such substances include:

(1) starch (modified or natural form),
(2) high molecular weight amine,
(3) protein,
(4) a polymer containing amide groups,
(5) poly(vinyl alcohol),
(6) partially hydrolyzed poly(vinyl acetate),
(7) an addition polymer containing a carboxyl group,
(8) carboxymethyl cellulose,
(9) poly(alkene ether), etc.

The following examples are included for a better understanding of this invention.

EXAMPLE 1

A mixture of 48.5 grams (0.25 mole) of dimethyl isophthalate, 24.2 grams (0.125 mole) of dimethyl terephthalate, 15 grams (0.075 mole) of hexahydroisophthalic acid, 14.8 grams (0.05 mole) of dimethyl 5-sodiosulfoisophthalate, 68.9 grams (0.65 mole) of diethylene glycol, and 0.8 ml. of a 21 percent catalyst solution of titanium isopropoxide is stirred and heated at 200° C. and a vacuum of 0.3 mm. is applied. Heating and stirring is continued for one hour under these conditions. After cooling the polymer obtained has an I.V. of 0.53 and is tough and rubbery. It is dissipated in hot water to the extent of about 20 weight percent to give a clear, slightly viscous solution. After storage of the solution for three months at room temperature, the water is evaporated from a portion. The residual polymer has an I.V. of 0.54. No measurable hydrolysis has occurred.

EXAMPLE 2

A polyester is made by the general procedure of Example 1 from the following:

82 mole percent isophthalic acid
18 mole percent 5-sodiosulfoisophthalic acid
57 mole percent diethylene glycol
43 mole percent 1,4-cyclohexanedimethanol The polyester has an I.V. of 0.22 and is mixed as a 5% solids solution with a mixture of solvents containing 50% ethanol and 50% water. The solution is applied as a spray to hair clippings arranged in a predetermined fashion. After evaporation of solvent, it is noted that the texture, hand, and ability to maintain arrangement under conditions simulating those of active persons were all good and at least duplicated those of commercially available grooming compositions. In addition, the composition has no noticeable odor. The composition readily dissolves in warm neutral pH water. Carbowax 600 in the amount of 10% by weight of the polyester is used. The initial glass transition temperature (Tg) of the polyester is 53° C., and with the addition of the Carbowax, the Tg is lowered to 43° C.

EXAMPLE 3

A polyester is made by the general procedure of Example 1 in accordance with the following formulation:

90 mole percent isophthalic acid
10 mole percent 5-sodiosulfoisophthalic acid
70 mole percent diethylene glycol
30 mole percent 1,4-cyclohexanedimethanol The polyester is mixed as a 10% solids solution with a mixture of solvents containing 25% isopropyl alcohol and 75% water. The solution is applied as a spray to hair, and results similar to those described for Example 2 are observed.

EXAMPLE 4

A polyester is made by the general procedure of Example 1 in accordance with the following formulation:

85 mole percent isophthalic acid
15 mole percent 5-sodiosulfoisophthalic acid
60 mole percent diethylene glycol
40 mole percent ethylene glycol The polyester is mixed as a 5% solids solution with a mixture of solvents containing 50% n-propyl alcohol and 50% water. The solution is applied as a spray to hair, and results similar to those described for Example 2 are observed.

EXAMPLE 5

A polyester is made by the general procedure of Example 1 in accordance with the following formulation:

80 mole percent isophthalic acid
20 mole percent 5-sodiosulfoisophthalic acid
55 mole percent diethylene glycol
45 mole percent 1,4-cyclohexanedimethanol The polyester is mixed as a 5% solids solution with a mixture of solvents containing 30% ethyl alcohol and 70% water, and modified with 5% Carbowax 600 poly-ethylene glycol. The solution is applied as a spray to hair, and results similar to those described for Example 2 are observed.

Carbowax 600 in the amount of 10% by weight of the polyester is used. The initial Tg of the polyester is 53° C., and with the addition of the Carbowax, the Tg is lowered to 43° C.

All percentages, ratios, etc., are on a weight basis unless otherwise specified.

The invention has been described in detail with particular reference to preferred embodiments thereof, but it will be understood that variations and modifications can be effected within the spirit and scope of the invention as described hereinabove and as defined in the appended claims.

We claim:

1. Method for grooming hair comprising applying to the hair an effective amount of a linear, water-dissipatible polyester in a solution of water and alcohol, said polyester being derived essentially from components
   (A) at least one dicarboxylic acid,
   (B) at least one diol, at least 20 mole percent of said diol component being a poly(ethylene glycol) having the formula

   $H{-}(OCH_2CH_2)_n{-}OH$ wherein n is an integer of from two to about ten, and
   (C) at least one difunctional dicarboxylic acid sulfo-monomer containing a —SO$_3$M group attached to an aromatic nucleus, wherein M is hydrogen or Na+, Li+, or K+, or a combination thereof, said sulfo-monomer component constituting at least about 8 mole percent to about 45 mole percent of the sum of the moles of said components (A) and (C), the acid components and the diol components of said polyester being substantially equimolar and said polyester having an I.V. of at least 0.15, as measured at 25° C. using 0.25 gram of polymer per 100 ml. of a solvent composed of 60 percent phenol and 40 percent tetrachloroethane.

2. Method of grooming hair comprising the steps of
   (A) arranging the hair in a predetermined fashion,
   (B) applying an effective amount of a polyester derived essentially from components
      (1) at least one dicarboxylic acid,
      (2) at least one diol, at least 20 mole percent of said diol component being a poly(ethylene glycol) having the formula

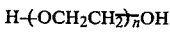
      $H{-}(OCH_2CH_2)_n{-}OH$ wherein n is an integer of from two to about ten, and
      (3) at least one difunctional dicarboxylic acid sulfo-monomer containing a —SO$_3$M group attached to an aromatic nucleus, wherein M is hydrogen or Na+, Li+, or K+, or a combination thereof, said sulfo-monomer component constituting at least about 8 mole percent to about 45 mole percent of the sum of the moles of said components (1) and (3), is a solution of water and alcohol to the hair, the acid components and the diol components of said polyester being substantially equimolar, and said polyester having an I.V. of at least 0.15, as measured at 25° C. using 0.25 gram of polymer per 100 ml. of a solvent composed of 60 percent phenol and 40 percent tetrachloroethane, and (C) allowing said water and alcohol to evaporate.

3. Method of grooming hair comprising the steps of
(A) arranging the hair in a predetermined fashion,
(B) applying an effective amount of a polyester derived essentially from isophthalic acid, 5-sodiosulfoisophthalic acid, diethylene glycol and 1,4-cyclohexanedimethanol in a solution of water and an alcohol selected from ethyl and isopropyl alcohol to the hair, the acid components and the diol components of said polyester being substantially equimolar and said polyester having an I.V. of at least 0.15, as measured at 25° C. using 0.25 gram of polymer per 100 ml. of a solvent composed of 60 percent phenol and 40 percent tetrachloroethane, and (C) allowing said water and alcohol to evaporate.

* * * * *